(12) United States Patent
Devoto et al.

(10) Patent No.: US 7,618,779 B2
(45) Date of Patent: Nov. 17, 2009

(54) CHROMOSOME 1P36 POLYMORPHISMS AND LOW BONE MINERAL DENSITY

(75) Inventors: Marcella Devoto, Philadelphia, PA (US); Katia Sol-Church, Wilmington, DE (US); Loretta D. Spotila, Haddonfield, NJ (US)

(73) Assignee: The Nemours Foundation, Wilmington, DE (US)

( * ) Notice: Subject to any disclaimer, the term of this patent is extended or adjusted under 35 U.S.C. 154(b) by 237 days.

(21) Appl. No.: 11/232,609

(22) Filed: Sep. 22, 2005

(65) Prior Publication Data

US 2007/0065836 A1 Mar. 22, 2007

(51) Int. Cl.
*C12Q 1/68* (2006.01)
(52) U.S. Cl. ......................................................... 435/6
(58) Field of Classification Search ........................ None
See application file for complete search history.

(56) References Cited

U.S. PATENT DOCUMENTS

| 6,762,023 | B1 | 7/2004 | Spotila | ........................... 435/6 |
| 6,825,336 | B1 | 11/2004 | Venter | ...................... 536/24.31 |

OTHER PUBLICATIONS

GeneCard for WDR8, last updated Aug. 21, 2007 URL: http://www.genecards.org/cgi-bin/carddisp.pl?gene=WDR8&ortholog=all&snp=87#ort.*
Koshizuka, Genomics vol. 72, Issue 3, Mar. 15, 2001, pp. 252-259.*
Mouse Genome Informatics, last database update Sep. 29, 2007 URL:http://www.informatics.jax.org/searches/snp_report.cgi?_Marker_key=48073.*
Hirschhorn et al. Genetics in Medicine. vol. 4, No. 2, pp. 45-61, Mar. 2002.*
Ioannidis. Nature Genetics, vol. 29, pp. 306-309, Nov. 2001.*
ReferenceSNP No. Rs2794328, http://www.ncbi.nlm.nih.gov/SNP/snp_ref.cgi?rs=2794328, Build 121, Entry date Mar. 18, 2004.*
Van Meurs et al 2003 Human Molecular Genetics vol. 12 p. 1745.*
Finkelstein 2002 Journal of Clincal Endocriniology Metabolism vol. 87 p. 3057.*
Ioannidis 2007 Journal of Bone and mineral research vol. 22 p. 173.*
Devoto et al., 1998, Eur. J. Hum. Genet. 6:151-157.
Devoto et al, 2001, Hum. Mol. Genet. 10:2447-2452.
Devoto et al, 2005, Eur. J. Hum. Genet. 13:781-788.
Wilson et al., 2003, Am. J. Hum. Genet. 72:144-155.
Frenck Holbrook et al, J. Biomol. Techn. 16:125-133 (2005).
Abecasis et al, 2000, Eur. J. Hum. Genet. 8(7):545-51.
Abecais et al., 2000, Am. J. Hum. Genet. 66(1):279-292.
NCBI dbSNP Accession No. rs446529 [online]. [retrieved on Oct. 12, 2005]. Retrieved from the Internet: <URL: http://www.ncbi.nlm.nih.gov/entrez/query.fcgi?db=snp&cmd=search&term=rs446529>.

NCBI dbSNP Reference SNP Cluster Report:rs446529 [online]. [retrieved on Oct. 12, 2005]. Retrieved from the Internet: <URL: http://www.ncbi.nlm.nih.gov/SNP/snp_ref.cgi?rs=446529>.
NCBI dsSNP Accession No. rs397559 [online]. [retrieved on Oct. 12, 2005]. Retrieved from the Internet: <URL:http://www.ncbi.nlm.nih.gov/entrez/query.fcgi?db=snp&cmd=search&term=rs397559>.
NCBI dbSNP Reference SNP Cluster Report:rs397559 [online]. [online]. [retrieved on Oct. 12, 2005]. Retrieved from the Internet: <URL: http://www.ncbi.nlm.nih.gov/SNP/snp_ref.cgi?rs=397559>.
NCBI dbSNP Accession No. rs2794328 [online]. [retrieved on Oct. 12, 2005]. Retrieved from the Internet <URL: http://www.ncbi.nlm.nih.gov/entrez/query.fcgi?db=snp&cmd=search&term=rs2794328>.
NCBI dbSNP Reference SNP Cluster Report:rs2794328 [online]. [online]. [retrieved on Oct. 12, 2005]. Retrieved from the Internet: <URL: http://www.ncbi.nlm.nih.gov/SNP/snp_ref.cgi?rs=2794328>.
NCBI dbSNP Accession No. rs1802353 [online]. [retrieved on Oct. 12, 2005]. Retrieved from the Internet: <URL: http://www.ncbi.nlm.nih.gov/entrez/query.fcgi?db=snp&cmd=search&term=rs1802353>.
NCBI dbSNP Reference SNP Cluster Report:rs1802353 [online]. [online] [retrieved on Oct. 12, 2005]. Retrieved from the Internet: <URL: http://www.ncbi.nlm.nih.gov/SNP/snp_ref.cgi?rs=1802353>.
Applied Biosystems Product Bulletin # 127PB12-01. 'TaqMan® SNP Genotyping Assays' 2004, [online], [retrieved Oct. 12, 2005]. Retrieved from the Applied Biosystems company website using Internet: http://doc.appliedbiosystems.com/search-dodnum.taf?dodnum=113945.
Applied Biosystems TaqMan® SNP Genotyping Assays, dbSNP rs2794328, [online], [retrieved Oct. 12, 2005] Retrieved from the Internet URL:http://myscience.appliedbiosystems.com/common/search.jsp?assayType=genotyping.
Applied Biosystems TaqMan® SNP Genotyping Assays, dbSNP rs446529, [online], [retrieved Oct. 12, 2005] Retrieved from the Internet, URL:http://myscience.appliedbiosystems.com/common/search.jsp?assayType=genotyping.
Applied Biosystems TaqMan® SNP Genotyping Assays, dbSNP rs397559, [online], [retrieved Oct. 12, 2005] Retrieved from the Internet URL:http://myscience.appliedbiosystems.com/common/search.jsp?assayType=genotyping.
Applied Biosystems TaqMan® SNP Genotyping Assays, dbSNP rs1802353, [online], [retrieved Oct. 12, 2005] Retrieved from the Internet URL:http://myscience.appliedbiosystems.com/common/search.jsp?assayType=genotyping.

* cited by examiner

*Primary Examiner*—Sarae Bausch
*Assistant Examiner*—Katherine Salmon
(74) *Attorney, Agent, or Firm*—Daniel A. Monaco; Drinker Biddle & Reath LLP

(57) ABSTRACT

The invention provides methods and compositions for diagnosing risk of low BMD and risk of osteoporosis based on the detection of SNP identity for human chromosome 1p36 polymorphisms designated in the NCBI SNP database (dbSNP) as rs2794328, rs446529, rs397559 and rs1802353.

4 Claims, No Drawings

SEQUENCE LISTING

```
<160> NUMBER OF SEQ ID NOS: 29

<210> SEQ ID NO 1
<211> LENGTH: 51
<212> TYPE: DNA
<213> ORGANISM: Homo sapiens
<220> FEATURE:
<221> NAME/KEY: allele
<222> LOCATION: (26)...(26)
<223> OTHER INFORMATION: an allele of NCBI dbSNP Accession no. rs2794328

<400> SEQUENCE: 1
gagggacctg agcggcagct ccaccatcag agccctccc ccacccttc c            51

<210> SEQ ID NO 2
<211> LENGTH: 425
<212> TYPE: DNA
<213> ORGANISM: Homo sapiens

<400> SEQUENCE: 2
agccccgtga agaccagccc tccgttctcc tgcagccagc accagcccac acgggctcca    60
acgctgggga gctggttcac gcagggcggg ggtcgtcatg gtaacgagcc ccccccccc   120 ccccggggcc cactcctctg ccttctgcag ccaccagctc acagtggagg ccacggctca  180
gggagtgtgg gcctggcagg agggacctga gcggcagctc caccmtcaga gccctcccc   240 cacccttcc ttctcaggga ccttgctctg cagagcgcgg gagcccctt attcaaaggg    300 cccccggccg ggtttgtcag ggaagtaccc actgaggggg ctgaaggcaa gacccctgaa   360
tacccgggcg ccctctcagc tgtactcaca gcctcaccta ctctgggccg ggccgggctg  420
gagca                                                               425

<210> SEQ ID NO 3
<211> LENGTH: 51
<212> TYPE: DNA
<213> ORGANISM: Homo sapiens
<220> FEATURE:
<221> NAME/KEY: allele
<222> LOCATION: (26)...(26)
<223> OTHER INFORMATION: an allele of NCBI dbSNP Accession no. rs446529

<400> SEQUENCE: 3
ggagcgtgtg ggagggaggg tgcgatgtgc atcagtgggg tgagaacgcc t            51
```

<210> SEQ ID NO 4
<211> LENGTH: 401
<212> TYPE: DNA
<213> ORGANISM: Homo sapiens

<400> SEQUENCE: 4

| aaagcctgcc acagcacgca aggcatggtg ggaccaggcc tcctggctgc tagaagaaga | 60 |
| caagaaaagc atactgggct gaagtcactt caaaagctgg tcacagcagg tcttttcttc | 120 |
| cgtgacactc ataggggga gatggggaga gaagtcatcc ctggaattcc agcctggagc | 180 |
| gtgtgggagg gagggtgcga ygtgcatcag tggggtgaga acgcctattg ggagagggga | 240 |
| ccaatttggg ccccaggttt gggactctcc tggttgaatg tctcgcccat ccaattttgc | 300 |
| aggaaaggag cctggtatgc aggctcagca cccactgcac cgggtgggca gctttattct | 360 |
| gcctgtggca ctggcctaag agctcagaaa ggtttaaaaa g | 401 |

<210> SEQ ID NO 5
<211> LENGTH: 51
<212> TYPE: DNA
<213> ORGANISM: Homo sapiens
<220> FEATURE:
<221> NAME/KEY: allele
<222> LOCATION: (26)...(26)
<223> OTHER INFORMATION: an allele of NCBI dbSNP Accession no. rs397559

<400> SEQUENCE: 5

| tattcaattc agcaatgtgt ctaagcgttt ctgtttgcca caagggcga a | 51 |

<210> SEQ ID NO 6
<211> LENGTH: 626
<212> TYPE: DNA
<213> ORGANISM: Homo sapiens

<400> SEQUENCE: 6

| atggacaggg cctggcttcc ttccgcctgt aacccatttc atagtcatta tattcaattc | 60 |
| agcaatgtgt ctaagygttt ctgtttgcca caagggcga atatgcaggc ttggccttcg | 120 |
| ccaaggcgtg tggccacacc atggaggggg cccgtgagca gaggctgccc atctgtgccc | 180 |
| ccctacagtc atgccataca taaagtgccc actctgggat tcttggggtc ctgtaggcca | 240 |
| ggagtcacaa acttttccta aaggactaga tgtacatatt tgagatttac aggttgtgca | 300 |
| gtctccatgt gaaatgtgca ttgagatcat ggccccgaag ggtgctgttg ggtgattcat | 360 |
| gatcttgcaa acgtgaagtg agggctctgt gccccttga ccctaactga acccccaggg | 420 |
| tgcccgaacc tttggaaagc cttttaactc agagggtaaa tctcactgcc agtgaattca | 480 |
| tttcccaagc tctctaccca cctcgtcctc accccattcc cggtgcccct gctgagaatc | 540 |
| ccagatttga atgcagcagt gctgagattt tgccaagaag atggccctga gaaggaaagg | 600 |
| tggattgatg ccttggttta ggcttg | 626 |

<210> SEQ ID NO 7
<211> LENGTH: 51
<212> TYPE: DNA
<213> ORGANISM: Homo sapiens
<220> FEATURE:
<221> NAME/KEY: allele
<222> LOCATION: (26)...(26)
<223> OTHER INFORMATION: an allele of NCBI dbSNP Accession no. rs1802353

<400> SEQUENCE: 7 accttcatt taaccgaaaa acacaaaccg ctttaacctc tttatttctg t         51

<210> SEQ ID NO 8
<211> LENGTH: 401
<212> TYPE: DNA
<213> ORGANISM: Homo sapiens

<400> SEQUENCE: 8
ccctccagag ttacctgggg aggaccgagg ccacacgcca ctgccccga ggccagagtg    60 taagtaaagg ataaccagga ctcgctggga gagatggact ctgtcctcag caacactcca   120
cagcagaaag gggtagcagg taccccttct tatcagcggt aaaaatgcat ttacaaacctt  180 tcatttaacc gaaaaacaca raccgcttta acctctttat ttctgtcccc cactgcatga   240
acatctatac aattttaaaa atacttcctc ataggatgct ttggcccttc atctatttaa   300
tcatagctac atacctattt tttataagta gcagtacaca ttcaaagggg tattcctagc   360
tcaatgcttg gtgttctagt tcaactttta tcctgcagca a                     401

<210> SEQ ID NO 9
<211> LENGTH: 19
<212> TYPE: DNA
<213> ORGANISM: Artificial Sequence
<220> FEATURE:
<223> OTHER INFORMATION: primer

<400> SEQUENCE: 9
caaggaccag acggttatc                                             19

<210> SEQ ID NO 10
<211> LENGTH: 19
<212> TYPE: DNA
<213> ORGANISM: Artificial Sequence
<220> FEATURE:
<223> OTHER INFORMATION: primer

<400> SEQUENCE: 10
gatccactcc agcagtcag                                             19

<210> SEQ ID NO 11
<211> LENGTH: 18
<212> TYPE: DNA
<213> ORGANISM: Artificial Sequence
<220> FEATURE:
<223> OTHER INFORMATION: primer

<400> SEQUENCE: 11
agacggtctc tgatgatg                                              18

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
tgcactggtt cccaccttc                                             20

<210> SEQ ID NO 13
<211> LENGTH: 19
<212> TYPE: DNA
<213> ORGANISM: Artificial Sequence
<220> FEATURE:
<223> OTHER INFORMATION: primer

<400> SEQUENCE: 13
ttgttgtcca cgtacagcg                                                  19

<210> SEQ ID NO 14
<211> LENGTH: 16
<212> TYPE: DNA
<213> ORGANISM: Artificial Sequence
<220> FEATURE:
<223> OTHER INFORMATION: primer

<400> SEQUENCE: 14
acagacttga tgccca                                                     16

<210> SEQ ID NO 15
<211> LENGTH: 20
<212> TYPE: DNA
<213> ORGANISM: Artificial Sequence
<220> FEATURE:
<223> OTHER INFORMATION: primer

<400> SEQUENCE: 15
gtgagcgtct gtgtgtaatg                                                 20

<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16
ggcaggatta caatgattcc                                                 20

<210> SEQ ID NO 17
<211> LENGTH: 18
<212> TYPE: DNA
<213> ORGANISM: Artificial Sequence
<220> FEATURE:
<223> OTHER INFORMATION: primer

<400> SEQUENCE: 17
ctaaatgata ctgcagtt                                                   18

<210> SEQ ID NO 18
<211> LENGTH: 19
<212> TYPE: DNA
<213> ORGANISM: Artificial Sequence
<220> FEATURE:
<223> OTHER INFORMATION: primer

<400> SEQUENCE: 18
ctggtgtacg tggtcgagg                                                  19

<210> SEQ ID NO 19
<211> LENGTH: 19
<212> TYPE: DNA
<213> ORGANISM: Artificial Sequence
<220> FEATURE:
<223> OTHER INFORMATION: primer

<400> SEQUENCE: 19
cttggagttg ttctctgcg                                                  19

<210> SEQ ID NO 20

```
<211> LENGTH: 16
<212> TYPE: DNA
<213> ORGANISM: Artificial Sequence
<220> FEATURE:
<223> OTHER INFORMATION: primer

<400> SEQUENCE: 20
gggcggggcg gcgggt                                                         16

<210> SEQ ID NO 21
<211> LENGTH: 19
<212> TYPE: DNA
<213> ORGANISM: Artificial Sequence
<220> FEATURE:
<223> OTHER INFORMATION: primer

<400> SEQUENCE: 21
aagtcagaag gcggaagtg                                                      19

<210> SEQ ID NO 22
<211> LENGTH: 22
<212> TYPE: DNA
<213> ORGANISM: Artificial Sequence
<220> FEATURE:
<223> OTHER INFORMATION: primer

<400> SEQUENCE: 22
acgtgggcgt ttcctttaaa gc                                                  22

<210> SEQ ID NO 23
<211> LENGTH: 16
<212> TYPE: DNA
<213> ORGANISM: Artificial Sequence
<220> FEATURE:
<223> OTHER INFORMATION: primer

<400> SEQUENCE: 23
caatgccgcg cggaag                                                         16

<210> SEQ ID NO 24
<211> LENGTH: 20
<212> TYPE: DNA
<213> ORGANISM: Artificial Sequence
<220> FEATURE:
<223> OTHER INFORMATION: primer

<400> SEQUENCE: 24
ccgacagagc aaacccgaaa                                                     20

<210> SEQ ID NO 25
<211> LENGTH: 21
<212> TYPE: DNA
<213> ORGANISM: Artificial Sequence
<220> FEATURE:
<223> OTHER INFORMATION: primer

<400> SEQUENCE: 25
caggacacag taaagggtga g                                                   21

<210> SEQ ID NO 26
<211> LENGTH: 16
<212> TYPE: DNA
<213> ORGANISM: Artificial Sequence
<220> FEATURE:
<223> OTHER INFORMATION: primer

<400> SEQUENCE: 26
```

```
ccagcattcc tatgcc                                                    16

<210> SEQ ID NO 27
<211> LENGTH: 20
<212> TYPE: DNA
<213> ORGANISM: Artificial Sequence
<220> FEATURE:
<223> OTHER INFORMATION: primer

<400> SEQUENCE: 27
cccctttcgc agacatcata                                                20

<210> SEQ ID NO 28
<211> LENGTH: 22
<212> TYPE: DNA
<213> ORGANISM: Artificial Sequence
<220> FEATURE:
<223> OTHER INFORMATION: primer

<400> SEQUENCE: 28
gaccacagtg actcaagaca ac                                             22

<210> SEQ ID NO 29
<211> LENGTH: 16
<212> TYPE: DNA
<213> ORGANISM: Artificial Sequence
<220> FEATURE:
<223> OTHER INFORMATION: primer

<400> SEQUENCE: 29
cagacccctt ccagcc                                                    16
```

CHROMOSOME 1P36 POLYMORPHISMS AND LOW BONE MINERAL DENSITY

FIELD OF THE INVENTION

The invention relates to methods of diagnosing risk of low bone mineral density and risk of osteoporosis. More particularly, the invention relates to the discovery of specific single nucleotide polymorphisms on human chromosome 1p36 that are linked to an elevated susceptibility for having or developing low bone mineral density and/or osteoporosis.

BACKGROUND OF THE INVENTION

Osteoporosis is a disease characterized by reduced skeletal strength, due to low bone mass and deterioration of bone tissue, leading to enhanced fragility and increased fracture risk. Osteoporosis is responsible for over 1.5 million fractures in the United States. The majority of such fractures are of the hip, spine and wrist. Unfortunately, the bone loss of osteoporosis occurs without symptoms. In many instances, the first sign of osteoporosis is the occurrence of a fracture.

Low bone mineral density (BMD) is one of the major risk factors for osteoporosis and is readily measured. Thus, monitoring BMD has become the main method of assessing risk of osteoporosis. In addition, there are a variety of treatments available to slow or stop on-going loss of BMD. Slowing or stopping on-going loss of BMD may contribute to delaying or warding off the development of osteoporosis. Thus, assessing BMD, particularly at an early stage of BMD loss, is extremely helpful for prophylactic and interventional treatments.

Current technologies for assessing BMD are based on ultrasound, X-ray techniques or radioactivity. Each of these approaches, however, has drawbacks. Ultrasound methods are rapid, painless and do not expose individuals to potentially harmful X-rays or radioactivity. Disadvantageously, ultrasound methods are unable to assess BMD in hip or spine, which are the bones most likely to fracture. X-ray techniques, such as dual-energy X-ray absorptiometry (DEXA) and peripheral dual-energy X-ray absorptiometry (P-DEXA), while rapid and able to measure BMD in hip and spine, expose individuals to X-rays and are also expensive. Dual photon absorptiometry also can measure BMD in hip and spine, but requires the individual to be injected with a radioactive substance. Furthermore, none of these methods for measuring BMD is capable of predicting the risk of developing low BMD in individuals.

There are a number of factors known to raise an individual's risk of having low BMD. Some these include: diet low in calcium, cigarette smoking, and use of corticosteroids and excessive intake of alcohol. Osteoporosis also runs in families, indicating a genetic component. Indeed, epidemiological studies support the hypothesis that a large part of the variation in BMD is caused by genetic susceptibility factors.

Linkage analyses and other research have further supported this hypothesis, and have revealed that there appear to be many genes involved in susceptibility. For instance, in a first-stage autosomal genome screen, Devoto et al. (1998, Eur. J. Hum. Genet. 6:151-157) identified regions on three different chromosomes, 1p, 2p and 4q, that appear linked to spine and hip BMD. Each of these regions contains many candidate genes. Subsequent work by this group further narrowed the region on 1p to 1p36.2-1p36.3 (Devoto et al, 2001, Hum. Mol. Genet. 10:2447-2452). While narrowed, this region still encompasses many genes. Bivariate variance component linkage analysis provides additional support for the linkage of 1p36 to BMD (Devoto et al, 2005, Eur. J. Hum. Genet. 13:781-788). Linkage studies by Wilson et al. (2002, Am. J. Hum. Genet. 72:114-155) provide independent support for the association of 1p36 with BMD and also identify 3p21 as another region linked to BMD.

Polymorphisms are allelic variants that occur in a population. A single nucleotide polymorphism (SNP) is a position in a particular DNA sequence characterized by the presence in a population of two, three or four different nucleotides at that position. The most common SNPs have two different nucleotides and are thus biallelic. Identification of SNPs associated with disease susceptibility is invaluable for screening and early initiation of prophylactic treatments. Furthermore, SNP identification may eventually lead to identifying genes that contribute to the development of low BMD and osteoporosis, which could aid the development of new therapeutic agents and treatment strategies.

There are several examples of specific SNPs that are correlated with elevated risk of low BMD. For instance, in US patent publication 2003/0235847, methods for determining risk of low BMD by assessing the nucleotide identity of one or more polymorphisms in the sclerostin gene on chromosome 17 are disclosed. Similarly, US patent publication number 2003/0176344 discloses methods for determining susceptibility to osteoporosis by assessing the nucleotide identity of one or more polymorphisms in the BMP2 gene on chromosome 20. U.S. Pat. No. 5,998,137 discloses methods for determining susceptibility to osteoporosis by assessing the nucleotide identity of one or more polymorphisms in the promoter of the TGF beta 1 gene. U.S. Pat. No. 6,825,336 discloses methods of determining susceptibility to osteoporosis by assessing the nucleotide identity of one or more single nucleotide polymorphisms in genes already known to be associated with osteoporosis. Reneland et al. (2005, BMC Medical Genetics 6:9) teach an association between specific SNP variants in the phosphodiesterase 4D locus on chromosome 5 and low BMD. U.S. Pat. No. 6,762,023 discloses methods for determining susceptibility to osteoporosis by assessing the nucleotide identity of one or more polymorphisms in the TNF alpha 2 receptor gene on chromosome 1.

There is, however, no evidence that the SNPs identified to date as associated with low BMD and/or osteoporosis are sufficient to identify all individuals at risk. Given that multiple genes appear to be involved in low BMD susceptibility, there is an on-going need in the art for identifying SNPs that are linked to low BMD. Furthermore, there is need in the art for a method of assessing risk of low BMD and therefore of elevated risk of osteoporosis, which does not require patient exposure to X-rays or radioactivity. This invention meets these needs.

SUMMARY OF THE INVENTION

According to one embodiment of the invention, there is provided a method of diagnosing risk of low bone mineral density (BMD) in an individual. The method comprises detecting the identity of at least one chromosome 1p36 polymorphism in a biological sample from an individual, wherein the at least one chromosome 1p36 polymorphism is selected from the group consisting of a polymorphism at nucleotide 26 of SEQ ID NO: 1 (rs2794328) or its corresponding minus strand, a polymorphism at nucleotide 26 of SEQ ID NO: 3 (rs446529) or its corresponding minus strand, a polymorphism at nucleotide 26 of SEQ ID NO: 5 (rs397559) or its corresponding minus strand, and a polymorphism at nucleotide 26 of SEQ ID NO: 7 (rs1802353) or its corresponding minus strand, wherein the presence of "A" at nucleotide 26 of SEQ ID NO. 1 or the presence of "T" at nucleotide 26 of the corresponding minus strand of SEQ ID NO: 1, the presence of "T" at nucleotide 26 of SEQ ID NO: 3 or the presence of "A" at nucleotide 26 of the corresponding minus strand of SEQ ID NO: 3, the presence of "C" at nucleotide 26 of SEQ ID NO: 5 or the presence of "G" at nucleotide 26 of the corresponding minus strand of SEQ ID NO: 5, or the presence of "A" at nucleotide 26 of SEQ ID NO: 7 or the presence of "T" at nucleotide 26 of the corresponding minus strand of SEQ ID NO: 7 is indicative of an elevated risk of low BMD in said individual.

According to another embodiment of the invention, the low BMD is femoral neck BMD and the at least one chromosome 1p36 polymorphism is selected from the group consisting of the polymorphism at nucleotide 26 of SEQ ID NO: 1 or its corresponding minus strand, the polymorphism at nucleotide 26 of SEQ ID NO: 3 or its corresponding minus strand, and the polymorphism at nucleotide 26 of SEQ ID NO: 5 or its corresponding minus strand.

According to another embodiment of the invention, the low BMD is lumbar spine BMD and the at least one chromosome 1p36 polymorphism is selected from the group consisting of the polymorphism at position 26 of SEQ ID NO: 3 or its corresponding minus strand and the polymorphism at position 26 of SEQ ID NO: 7 or its corresponding minus strand.

According to another embodiment of the invention, the low BMD is trochanter BMD and the at least one chromosome 1p36 polymorphism is selected from the group consisting of the polymorphism at position 26 of SEQ ID NO: 1 or its corresponding minus strand and the polymorphism at position 26 of SEQ ID NO: 7 or its corresponding minus strand.

According to another embodiment of the invention, there is provided a method diagnosing risk of osteoporosis in an individual. The method comprises detecting the identity of at least one chromosome 1p36 polymorphism in a biological sample from an individual, wherein the at least one chromosome 1p36 polymorphism is selected from the group consisting of a polymorphism at nucleotide 26 of SEQ ID NO: 1 (rs2794328) or its corresponding minus strand, a polymorphism at nucleotide 26 of SEQ ID NO: 3 (rs446529) or its corresponding minus strand, a polymorphism at nucleotide 26 of SEQ ID NO: 5 (rs397559) or its corresponding minus strand, and a polymorphism at nucleotide 26 of SEQ ID NO: 7 (rs 802353) or its corresponding minus strand, wherein the presence of "A" at nucleotide 26 of SEQ ID NO. 1 or the presence of "T" at nucleotide 26 of the corresponding minus strand of SEQ ID NO: 1, the presence of "T" at nucleotide 26 of SEQ ID NO: 3 or the presence of "A" at nucleotide 26 of the corresponding minus strand of SEQ ID NO: 3, the presence of "C" at nucleotide 26 of SEQ ID NO: 5 or the presence of "G" at nucleotide 26 of the corresponding minus strand of SEQ ID NO: 5, or the presence of "A" at nucleotide 26 of SEQ ID NO: 7 or the presence of "T" at nucleotide 26 of the corresponding minus strand of SEQ ID NO: 7 is indicative of an elevated risk of osteoporosis in said individual.

According to another embodiment of the invention, a kit is provided for diagnosing risk of low bone mineral density (BMD). The kit comprises at least one pair of amplification primers for forming an amplified double-stranded target polynucleotide, wherein the pair is designed to amplify a target polynucleotide sequence comprising a chromosome 1p36 polymorphism selected from the group consisting of a polymorphism at nucleotide 26 of SEQ ID NO: 1 (rs2794328), a polymorphism at nucleotide 26 of SEQ ID NO: 3 (rs446529), a polymorphism at nucleotide 26 of SEQ ID NO: 5 (rs397559) and a polymorphism at nucleotide 26 of SEQ ID NO: 7 (rs1802353), at least one detection probe, wherein the detection probe hybridizes to a sequence 3' of the chromosome 1p36 polymorphism in either strand of the amplified double-stranded target polynucleotide, and an instructional material for performing the risk diagnosis. According to one embodiment, the detection probe hybridizes to a sequence immediately 3' to said chromosome 1p36 polymorphism. According to another embodiment of the invention, the kit further comprises a second pair of amplification primers for forming a second amplified double-stranded target polynucleotide, wherein the second pair is designed to amplify a target polynucleotide sequence comprising a second chromosome 1p36 polymorphism selected from the group consisting of the polymorphism at nucleotide 26 of SEQ ID NO: 1 (rs2794328), the polymorphism at nucleotide 26 of SEQ ID NO: 3 (rs446529), the polymorphism at nucleotide 26 of SEQ ID NO: 5 (rs397559) and the polymorphism at nucleotide 26 of SEQ ID NO: 7 (rs1802353), and a second detection probe, wherein the second detection probe hybridizes to a sequence 3' of the second chromosome 1p36 polymorphism in either strand of the amplified double-stranded target polynucleotide, and further wherein the second chromosome 1p36 polymorphism is different from the first chromosome 1p36 polymorphism.

According to a preferred embodiment of the invention, the kit comprises a first pair of amplification primers for forming a first amplified double-stranded target polynucleotide, wherein the first pair is designed to amplify a target polynucleotide sequence comprising the chromosome 1p36 polymorphism at position 26 of SEQ ID NO: 1 (rs2794328), a first detection probe, wherein the first detection probe hybridizes to a sequence 3' of the chromosome 1p36 polymorphism at position 26 of SEQ ID NO: 1 in either strand of the first amplified double-stranded target polynucleotide, a second pair of amplification primers for forming a second amplified double-stranded target polynucleotide, wherein the second pair is designed to amplify a target polynucleotide sequence comprising the chromosome 1p36 polymorphism at position 26 of SEQ ID NO: 3 (rs446529), a second detection probe, wherein the second detection probe hybridizes to a sequence 3' of the chromosome 1p36 polymorphism at position 26 of SEQ ID NO: 3 in either strand of the second amplified double-stranded target polynucleotide, a third pair of amplification primers for forming a third amplified double-stranded target polynucleotide, wherein the third pair is designed to amplify a target polynucleotide sequence comprising the chromosome 1p36 polymorphism at position 26 of SEQ ID NO: 5 (rs397559), a third detection probe, wherein the third detection probe hybridizes to a sequence 3' of the chromosome 1p36 polymorphism at position 26 of SEQ ID NO: 5 in either strand of the third amplified double-stranded target polynucleotide, a fourth pair of amplification primers for forming a fourth amplified double-stranded target polynucleotide, wherein the fourth pair is designed to amplify a target polynucleotide sequence comprising the chromosome 1p36 polymorphism at position 26 of SEQ ID NO: 7 (rs1802353), and a fourth detection probe, wherein the fourth detection probe hybridizes to a sequence 3' of the chromosome 1p36 polymorphism at position 26 of SEQ ID NO: 7 in either strand of the fourth amplified double-stranded target polynucleotide.

DEFINITIONS

The term "individual" includes human beings and non-human animals.

As used herein, "allele" refers to one or more alternative forms of a particular sequence that contains a SNP. The sequence may or may not be within a gene.

As used herein, "elevated risk of low BMD" refers to a greater likelihood of having or developing low bone marrow density (BMD) in an individual having a particular nucleotide at a particular SNP, compared to an individual that does not have that nucleotide at that SNP.

As used herein, "elevated risk of osteoporosis" refers to a greater likelihood of having or developing osteoporosis in an individual having a particular nucleotide at a particular SNP, compared to an individual that does not have that nucleotide at that SNP.

As used herein, "low BMD" is when an individual has a BMD value ("T-score") below the average BMD value determined by the same method at the same bone of a young adult of the same gender. Osteoporosis is diagnosed in an individual when he/she has a BMD value that is statistically greater than 2.5 standard deviations below the average BMD value determined by the same method at the same bone of a young adult of the same gender. BMD is preferably determined by DEXA or P-DEXA. The bone is preferably the hip, particularly the femoral neck, or the lumbar spine. Low BMD is also called "osteopenia".

"Amplification" refers to any means by which a polynucleotide sequence is copied and thus expanded into a larger number of polynucleotide sequences, e.g., by reverse transcription, polymerase chain reaction or ligase chain reaction, among others.

As used herein, an "instructional material" includes a publication, a recording, a diagram, or any other medium of expression which can be used to communicate the usefulness of the kit for its designated use in practicing a method of the invention. The instructional material of the kit of the invention may, for example, be affixed to a container which contains the composition or be shipped together with a container which contains the composition. Alternatively, the instructional material may be shipped separately from the container with the intention that the instructional material and the composition be used cooperatively by the recipient.

In the context of the present invention, the following abbreviations for the commonly occurring nucleic acid bases are used. "A" refers to adenosine, "C" refers to cytidine, "G" refers to guanosine, "T" refers to thymidine, and "U" refers to uridine.

A "polynucleotide" means a single strand or parallel and anti-parallel strands of a nucleic acid. Thus, a polynucleotide may be either a single-stranded or a double-stranded nucleic acid. A polynucleotide is not defined by length and thus includes very large nucleic acids, as well as short ones, such as an oligonucleotide.

The term "nucleic acid" typically refers to large polynucleotides.

The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand". Sequences on a DNA strand which are located 5' to a reference point on the DNA are referred to as "upstream sequences". Sequences on a DNA strand which are 3' to a reference point on the DNA are referred to as "downstream sequences."

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. Typical uses of primers include, but are not limited to, sequencing reactions and amplification reactions. A primer is typically single-stranded, but may be double-stranded. Primers are typically deoxyribonucleic acids, but a wide variety of synthetic and naturally-occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., detectable moieties, such as chromogenic, radioactive or fluorescent moieties, or moieties for isolation, e.g., biotin.

"Probe" refers to a polynucleotide that is capable of specifically hybridizing to a designated sequence of another polynucleotide. "Probe" as used herein encompasses oligonucleotide probes. A probe may or may not provide a point of initiation for synthesis of a complementary polynucleotide. A probe specifically hybridizes to a target complementary polynucleotide, but need not reflect the exact complementary sequence of the template. In such a case, specific hybridization of the probe to the target depends on the stringency of the hybridization conditions. For use in SNP detection, some probes are allele-specific, and hybridization conditions are selected such that the probe binds only to a specific SNP allele. Probes can be labeled with, e.g., detectable moieties, such as chromogenic, radioactive or fluorescent moieties, and used as detectable agents.

As used herein, "label" refers to a group covalently attached to a polynucleotide. The label may be attached anywhere on the polynucleotide but is preferably attached at one or both termini of the polynucleotide. The label is capable of conducting a function such as giving a signal for detection of the molecule by such means as fluorescence, chemiluminescence, and electrochemical luminescence. Alternatively, the label allows for separation or immobilization of the molecule by a specific or non-specific capture method (Andrus, 1995, In: PCR 2: A Practical Approach, McPherson et al. (eds) Oxford University Press, Oxford, England, pp. 39-54). Labels include, but are not limited to, fluorescent dyes, such as fluorescein and rhodamine derivatives (U.S. Pat. No. 5,188,934; U.S. Pat. No. 5,366,860), cyanine dyes, haptens, and energy-transfer dyes (Clegg, 1992, Meth. Enzymol. 211: 353-388; Cardullor et al., 1988, PNAS 85:8790-8794).

As used herein, "proband" refers to the first member in a family or pedigree through whom the family or pedigree came to medical/scientific attention.

DETAILED DESCRIPTION OF THE INVENTION

According to the present invention, certain single nucleotide polymorphisms (SNPs) on human chromosome 1p36 are associated with an elevated risk of having or developing low bone mineral density (BMD) and, consequently, with an elevated risk of having or developing osteoporosis. Therefore, the present invention provides methods of assessing risk of low BMD in an individual. The invention further provides methods of assessing risk of osteoporosis in an individual. Kits useful in practicing embodiments of the inventive methods are also provided.

The methods and compositions of the instant invention are applicable to any individual. The individual is a human. The inventive methods and compositions are particularly indicated for individuals having other risk factors for osteoporosis. Such individuals include postmenopausal females, and premenopausal females, perimenopausal females, and males with any of the following risk factors: thin or small frame; family history of osteoporosis; diet low in calcium; cigarette smoking; excessive use of alcohol; inactive lifestyle; use of corticosteroids or thyroid medication; low testosterone levels in men.

An individual determined to be at an elevated risk of having or developing low BMD, according to the method herein, may be prescribed one or more treatments intended to combat low BMD. Such treatment include, but are not limited to, diet changes, dietary supplements, including calcium and vitamin D, weight-bearing exercise and medication, including bisphosphonates, such as alendronate; calcitonin; and raloxifene. When an elevated risk of low BMD is determined in an individual according to the method of the invention, BMD may be directly assessed by any known method of measuring BMD. Such methods include but are not limited to DEXA, P-DEXA, ultrasound and dual photon absorptiometry. DEXA is the preferred method for measuring BMD. An individual at elevated risk of low BMD according to the method herein, who is found to have normal BMD, is a candidate for more frequent BMD screening, in addition to prophylactic treatments. Similarly, an individual determined to be an elevated risk of having or developing osteoporosis, according to the method herein, may be prescribed therapies to treat the osteoporosis, or prophylactic treatments to delay or preclude the onset of osteoporosis.

I. 1p36 SNPs of the Invention

Four SNPs located in human chromosome 1p36 are associated with an elevated risk of low BMD. Since low BMD is a risk factor for developing osteoporosis, the determination of risk of low BMD also indicates the risk of developing or having osteoporosis. The four SNPs for risk assessment according to the method of the invention are at position 26 of each of SEQ ID NOs: 1, 3, 5, and 7. The sequences 5' and 3' to the polymorphic site are referred to as "flanking sequences" or "context sequence". SEQ ID NOs: 1, 3, 5 and 7 contain the alleles that are associated with risk of low BMD and osteoporosis.

SEQ ID NO: 1 contains the sequence of one of the alleles of NCBI dbSNP accession number rs2794328. As shown in Table 1, the two alleles at this SNP position are A and C. The allele associated with an elevated risk of low BMD and osteoporosis has an A at position 26. SEQ ID NO: 3 contains the sequence for one of the alleles of NCBI dbSNP accession number rs446529. The two alleles at this SNP position are T and C. The allele associated with an elevated risk of low BMD and osteoporosis has a T at position 26. SEQ ID NO: 5 contains the sequence for one of the alleles of NCBI dbSNP accession number rs397559. The allele associated with an elevated risk of low BMD and osteoporosis has a C at position 26. SEQ ID NO: 7 contains the sequence for one of the alleles of NCBI dbSNP accession number rs1802353. The allele associated with an elevated risk of low BMD and osteoporosis has an A at position 26. Table 1 also lists the chromosome 1 basepair position of each SNP. The nucleotide identity of the two SNP alleles is shown in brackets, and the sequence of the 25 nucleotides immediately 5' and 3' to the SNP nucleotide is shown. Table 1 also lists the SNP nucleotide that is associated with low BMD, as discovered herein.

TABLE 1

| SNP ID[1] | Chromosome 1 location of SNP in bp[2] | SNP alleles and 25 nucleotide sequence 5' and 3' of SNP nucleotide | SNP elevated risk allele | SEQ ID NO: for diagnostic allele |
|---|---|---|---|---|
| rs2794328 | 3,538,553 | 5'-GAGGGACCTGAGCGGCAG CTCCACC[A/C]TCAGAGCCCC TCCCCCACCCCTTCC-3' | A | 1 |
| rs446529 | 4,705,787 | 5'-GGAGCGTGTGGGAGGGAG GGTGCGA[C/T]GTGCATCAGT GGGGTGAGAACGCCT-3' | T | 3 |
| rs397559 | 4,731,172 | 5'-TATTCAATTCAGCAATGTG TCTAAG[C/T]GTTTCTGTTTGC CACAAGGGGCGAA-3' | C | 5 |
| rs1802353 | 6,218,946 | 5'-ACCTTTCATTTAACCGAAA AACACA[A/G]ACCGCTTTAAC CTCTTTATTTCTGT-3' | A | 7 |

Note
[1]The rs number refers to the NCBI dbSNP accession number for the SNP.
Note
[2]Chromosomal location in bp determined from NCBI SNP database as of the Jun. 27, 2005 update, accessed on Jul. 7, 2005.

As used herein, SEQ ID NOS; 1, 3, 5 and 7 are the plus strand sequences of the four SNPs of the invention. For each plus strand, there is a minus strand sequence, which is the exact complement to the plus strand. For example, if the sequence of a plus strand is 5'-AGTGCCTA-3', the sequence of its corresponding minus strand is 5'-TAGGCACT-3'. A plus strand and its corresponding minus strand may base pair with each other when in the anti-parallel orientation. The identity of the nucleotide at position 26 in the minus strand sequence of each of the SNPs of the invention, therefore, is also predictive of risk of low BMD and osteoporosis. Specifically, the presence of a T at position 26 in the minus strand of SEQ ID NO: 1 is associated with an elevated risk of low BMD and osteoporosis. The presence of an A at position 26 in the minus strand of SEQ ID NO: 3 is associated with an elevated risk of low BMD and osteoporosis. The presence of a G at position 26 in the minus strand of SEQ ID NO: 5 is associated with an elevated risk of low BMD and osteoporosis. The presence of a T at position 26 in the minus strand of SEQ ID NO: 7 is associated with an elevated risk of low BMD and osteoporosis.

Additional flanking sequences for each of rs2794328, rs446529, rs397559 and rs1802353 are provided in SEQ ID NOs: 2, 4, 6 and 8, respectively. Specifically, SEQ ID NO: 2 contains SEQ ID NO: 1 and an additional 199 nucleotides 5' of the SEQ ID NO: 1 sequence and an additional 175 nucleotides 3' of the SEQ ID NO: 1 sequence. IN SEQ ID NO: 2. the SNP position is nucleotide 225 and is listed as "m", the symbol meaning the nucleotide is either A or C in DNA sequences. Similarly, SEQ ID NO: 4 contains SEQ ID NO: 3 and an additional 175 nucleotides 5' of the SEQ ID NO: 3 sequence and an additional 174 nucleotides 3' of the SEQ ID NO: 3 sequence. The SNP position in SEQ ID NO: 4 is nucleotide 201 and is listed as "y", the symbol meaning the nucleotide is either T or C in DNA sequences. SEQ ID NO: 6 contains SEQ ID NO: 5 and an additional 50 nucleotides 5' of the SEQ ID NO: 5 sequence and an additional 525 nucleotides 3' of the SEQ ID NO: 5 sequence. The SNP position is nucleotide 76 in SEQ ID NO: 6 and is listed as "y". SEQ ID NO: 8 contains SEQ ID NO: 7 and an additional 175 nucleotides 5' of the SEQ ID NO: 7 sequence and an additional 174 nucleotides 3' of the SEQ ID NO: 7 sequence. The SNP position in SEQ ID NO: 8 is nucleotide 76 and is listed as "r", the symbol meaning the nucleotide is either G or A. One of skill in the art can deduce the sequence of the corresponding minus strands for each of SEQ ID NOs: 2, 4, 6 and 8. This context sequence information is useful for designing oligonucleotide probes and primers for detecting the SNP identity according to the methods of the invention.

According to one embodiment of the invention, the 1p36 polymorphism at position 26 of SEQ ID NO: 1 or its corresponding minus strand is associated with the BMD in the femoral neck and in the trochanter. According to another embodiment, the 1p36 polymorphism at position 26 of SEQ ID NO: 3 or its corresponding minus strand is associated with the BMD in the femoral neck. According to another embodiment, the 1p36 polymorphism at position 26 of SEQ ID NO: 5 or its corresponding minus strand is associated with the BMD in the femoral neck and the lumbar spine. According to another embodiment, the 1p36 polymorphism at position 26 of SEQ ID No: 7 or its corresponding minus strand is associated with BMD in the lumbar spine and the trochanter.

It may be appreciated that some individuals may have one or more polymorphisms in the context sequence of a 1p36 polymorphism of the invention. For instance, an individual may have a polymorphism in the 3' flanking sequence of the polymorphism at nucleotide 26 of SEQ ID NO: 3 (rs446529). The methods of the invention, however, may still be practiced with this individual. In other words, the methods of the invention are not limited to those individuals whose flanking sequences are 100% identical to the flanking sequences for any of the polymorphisms at nucleotide 26 of SEQ ID NOs: 1, 3, 5 and 7.

Further, the detecting step may include the step of detecting whether the subject is heterozygous or homozygous for the polymorphism of interest. A person who is homozygous for the SNP allele associated with low BMD at any of the four SNP positions is at elevated risk of low BMD and osteoporosis. A person who is heterozygous at any of the four SNPs is also at elevated risk of low BMD and osteoporosis. A person who is homozygous at any of the four SNPs may be at an increased risk compared to a person who is heterozygous.

II. Identifying SNP Allele

The methods of the invention comprise identifying the nucleotide at one or more SNPs on chromosome 1p36 in a biological sample obtained from an individual.

A. Biological Sample

Biological samples useful in the practice of the methods of the invention can be any biological sample from which any of genomic DNA, mRNA, unprocessed RNA transcripts of genomic DNA or combinations of the three can be isolated. As used herein, "unprocessed RNA" refers to RNA transcripts which have not been spliced and therefore contain at least one intron. Such unprocessed RNA is suitable for detecting SNPs located in an intron, such as the SNP at position 26 in SEQ ID NO: 3 (rs446529) and SEQ ID NO: 5 (rs397559), or in 5' or 3' untranslated region ("UTR"), such as the SNP at position 26 in SEQ ID NO: 7 (rs1802353). Suitable biological samples include, but are not limited to, blood, buccal swabs, hair, bone, and tissue samples, such as skin or biopsy samples. Biological samples also include lymphoblast cultures established from an individuals lymphocytes by EBV transformation. In a preferred embodiment, the biological sample is blood.

Genomic DNA, mRNA, and/or unprocessed RNA transcripts are isolated from the biological sample by conventional means known to the skilled artisan. See, for instance, Sambrook et al. (2001, Molecular Cloning: A Laboratory Manual, Cold Spring Harbor Laboratory Press, Cold Spring Harbor, N.Y.) and Ausubel et al. (eds., 1997, Current Protocols in Molecular Biology, John Wiley & Sons, New York). The isolated genomic DNA, mRNA, and/or unprocessed RNA transcripts is used, with or without amplification, to detect the SNP allele at one or more of the chromosome 1p36 SNPs shown herein to be associated with low bone marrow density.

B. Amplification

Many SNP identification methods that can be used in the methods of the invention involve amplifying a target polynucleotide sequence prior to detecting the SNP identity. A "target polynucleotide sequence" is a region of the genomic DNA, mRNA or unprocessed RNA containing the SNP of interest. Some methods, including the 5' nuclease assay described in Section D, combine the amplification and detection processes in one step, as described elsewhere herein. Other methods, such as the invasive cleavage assay described in Section D, use signal amplification and are thereby sufficiently sensitive such that the genomic nucleic acid sample does not need to be amplified.

Amplification of a target polynucleotide sequence may be carried out by any method known to the skilled artisan. See, for instance, Kwoh et al., (1990, Am. Biotechnol. Lab. 8, 14-25) and Hagen-Mann, et al., (1995, Exp. Clin. Endocrinol. Diabetes 103:150-155). Amplification methods include, but are not limited to, polymerase chain reaction ("PCR") including RT-PCR, strand displacement amplification (Walker et al., 1992, PNAS 89, 392-396; Walker et al., 1992, Nucleic Acids Res. 20, 1691-1696), strand displacement amplification using Phi29 DNA polymerase (U.S. Pat. No. 5,001,050), transcription-based amplification (Kwoh et al., 1989, PNAS 86, 1173-1177), self-sustained sequence replication ("3SR") (Guatelli et al., 1990, PNAS 87, 1874-1878; Mueller et al., 1997, Histochem. Cell Biol. 108:431-437), the Q.beta. replicase system (Lizardi et al., 1988, BioTechnology 6, 1197-1202; Cahill et al., 1991, Clin., Chem. 37:1482-1485), nucleic acid sequence-based amplification ("NASBA") (Lewis, 1992, Genetic Engineering News 12 (9), 1), the repair chain reaction ("RCR") (Lewis, 1992, supra), and boomerang DNA amplification (or "BDA") (Lewis, 1992, supra). PCR is the preferred method of amplifying the target polynucleotide sequence.

PCR may be carried out in accordance with known techniques. See, e.g., Bartlett et al., eds., 2003, PCR Protocols Second Edition, Humana Press, Totowa, N.J. and U.S. Pat. Nos. 4,683,195; 4,683,202; 4,800,159; and 4,965,188. In general, PCR involves, first, treating a nucleic acid sample (e.g., in the presence of a heat stable DNA polymerase) with a pair of amplification primers. One primer of the pair hybridizes to one strand of a target polynucleotide sequence. The second primer of the pair hybridizes to the other, complementary strand of the target polynucleotide sequence. The primers are hybridized to their target polynucleotide sequence strands under conditions such that an extension product of each primer is synthesized which is complementary to each nucleic acid strand. The extension product synthesized from each primer, when it is separated from its complement, can serve as a template for synthesis of the extension product of the other primer. After primer extension, the sample is treated to denaturing conditions to separate the primer extension products from their templates. These steps are cyclically repeated until the desired degree of amplification is obtained.

The amplified target polynucleotide may be used in one of the detection assays described elsewhere herein to identify the SNP present in the amplified target polynucleotide sequence.

C. Oligonucleotide primers and probes

Nucleic acid amplification techniques, such as the foregoing, and SNP allele detection methods, as described below, may involve the use of a primer, a pair of primers, or two pairs of primers which specifically bind to nucleic acid containing the SNP to be detected, and do not bind to nucleic acid that does not contain the SNP to be detected under the same hybridization conditions. Such probes are sometimes referred to as "amplification primers" herein.

In some detection assays, a polynucleotide probe, which is used to detect DNA containing a SNP of interest, is a probe which binds to DNA encoding a specific SNP allele, but does not bind to DNA that does not encode that specific SNP allele under the same hybridization conditions. For instance, the detection probe used for 5' nuclease assay, described in Section D, straddles a SNP site and discriminates between alleles. In other assays, a polynucleotide probe which is used to detect DNA containing a SNP of interest is a probe that binds to either SNP allele at a sequence that does not include the SNP. This type of probe may bind to a sequence immediately 3' to the SNP or may bind to a sequence that is 3' to the SNP and removed from the SNP by one or more bases. In some cases, the polynucleotide probe is labelled with one or more labels, such as those, for instance, set forth elsewhere herein in the 5' nuclease assay. Polynucleotide probes as described above are sometimes referred to as "detection probes" or "detection primers" herein.

Probes and primers may be any suitable length, but are typically oligonucleotides from 5, 6, 8 or 12 nucleotides in length up to 40, 50 or 60 nucleotides in length, or more. The oligonucleotide typically comprises a region of nucleotide sequence that hybridizes under stringent conditions to at least about 5, 6, 8, 12, 20, 25, 40, 50 or more consecutive nucleotides in the target polynucleotide sequence. The skilled artisan knows where the region of consecutive nucleotides intended to hybridize to the target polynucleotide sequence must be located in the oligonucleotide, based on the intended use of the oligonucleotide. For instance, in an oligonucleotide for use in a primer extension assay, the skilled artisan knows the region of consecutive nucleotides must include the 3' terminal nucleotide. The probes and primers are typically substantially purified. Such probes and/or primers may be immobilized on or coupled to a solid support such as a bead, glass slide or chip in accordance with known techniques, and/or coupled to or labelled with a detectable label such as a fluorescent compound, a chemiluminescent compound, a radioactive element, or an enzyme in accordance with known techniques.

Probes and primers are designed using the sequences flanking the SNP in the target polynucleotide sequence. SEQ ID NOs: 1-8 provide flanking sequence information for each of the four SNPs of the invention. Depending on the particular SNP identification protocol utilized, the consecutive nucleotides of the region that hybridizes to a target polynucleotide sequence may include the target SNP position. Alternatively the region of consecutive nucleotides may be complementary to a sequence in close enough proximity 5' and/or 3' to the SNP position to carry out the desired assay. The skilled artisan can readily design primer and probe sequences using the sequences provided herein. Considerations for primer and probe design with regard to, for instance, melting temperature and avoidance of primer-dimers, are well known to the skilled artisan. In addition, a number of computer programs, such as Primer Express® (Applied Biosystems, Foster City, Calif.) and Primo SNP 3.4 (Chang Bioscience, Castro Valley, Calif.), can be readily used to obtain optimal primer/probe sets. The probes and primers may be chemically synthesized using commercially available reagents and synthesizers by methods that are well-known in the art (see, e.g., Herdwijn, 2004, Oligonucleotide Synthesis: Methods and Applications, Humana Press, Totowa, N.J.).

D. Methods of identifying SNP alleles

The process of identifying the nucleotide present at one or more of the SNP positions disclosed in Table 1 and the Sequence Listing is referred to herein by phrases including, but not limited to: "SNP identification", "SNP genotyping", "SNP typing", "SNP detection" and "SNP scoring".

The method of the invention can identify a nucleotide occurrence for either the plus or minus strand of DNA. That is, the invention encompasses not only identifying the nucleotide at the SNP position in the strand shown in SEQ ID NOs: 1, 3, 5 and/or 7, but also identifying the nucleotide at the SNP position in the corresponding complementary minus strand of in SEQ ID NOs: 1, 3, 5 and/or 7. For instance, for a SNP in which the allele associated with an elevated risk of low BMD or osteoporosis has a "C" at the SNP on the plus strand, detecting a "G" in the SNP position of the complementary, minus strand is also indicative of an elevated risk of low BMD or osteoporosis.

There are numerous methods of SNP identification known to the skilled artisan. See, for instance, Kwok (2001, Annu. Rev. Genomics Hum. Genet. 2:235-258) and Theophilus et al., (2002, PCR Mutation Detection Protocols, Humana Press, Totowa, N.J.). Any may be used in the practice of the present invention. SNP identification methods include, but are not limited to, 5' nuclease assay, primer extension or elongation assays, allele specific oligonucleotide ligation, allele specific hybridization, sequencing, invasive cleavage reaction, branch migration assay, single strand conformational polymorphism (SSCP), denaturing gradient gel electrophoresis (DGGE) and immunoassay. Many of these assays have or can be adapted for microarrays. See, for instance, Erdogan et al. (2001, Nuc. Acids Res. 29:e36); O'Meara et al. (2002, Nuc. Acids Res. 30:e75); Pastinen et al. (1997, Genome Res. 7:606-614); Pastinen et al. (2000, Genome Res.

10:1031-1042); and U.S. Pat. No. 6,294,336. Preferred SNP genotyping methods are the 5' nuclease assay, primer extension assays and sequencing.

The 5' nuclease assay, also known as the 5' nuclease PCR assay and the TaqMan™ Assay (Applied Biosystems, Foster City, Calif.), provides a sensitive and rapid means of genotyping SNPs. The 5' nuclease assay detects, by means of a probe, the accumulation of a specific amplified product during PCR. The probe is designed to straddle a target SNP position and hybridize to the target polynucleotide sequence containing the SNP position only if a particular SNP allele is present. During the PCR reaction, the DNA polymerase, which extends an amplification primer annealed to the same strand and upstream of the hybridized probe, uses its 5' nuclease activity and cleaves the hybridized probe. There are different ways to detect the probe cleavage. In one common variation, the 5' nuclease assay utilizes an oligonucleotide probe labeled with a fluorescent reporter dye at the 5' end of the probe and a quencher dye at the 3' end of the probe. See, for instance, Lee et al., (1993), Nuc. Acids Res. 21:3761-3766), Livak (1999, Genet. Anal. 14:143-149) and U.S. Pat. Nos. 5,538,848, 5,876,930, 6,030,787, 6,258,569 and 6,821,727. The proximity of the quencher dye to the fluorescent reporter in the intact probe maintains a reduced fluorescence for the reporter. Cleavage of the probe separates the fluorescent reporter dye and the quencher dye, resulting in increased fluorescence of the reporter. The 5' nuclease activity of DNA polymerase cleaves the probe between the reporter and the quencher only if the probe hybridizes to the target, and the target is amplified during PCR. Accumulation of a particular PCR product is thus detected directly by monitoring the increase in fluorescence of the reporter dye. In another variation, the oligonucleotide probe for each SNP allele has a unique fluorescent dye and detection is by means of fluorescence polarization (Kwok, 2002, Human Mutat. 19:315-323). This assay advantageously can detect heterozygotes.

The primer extension reaction (also called "mini-sequencing", "single base extension assay" or "single nucleotide extension assay", and "primer elongation assay") involves designing and annealing a primer to a sequence downstream of a target SNP position in an amplified target polynucleotide sequence ("amplified target"). A mix of dideoxynucleotide triphosphates (ddNTPs) and/or deoxynucleotide triphosphates (dNTPs) are added to a reaction mixture containing amplified target, primer, and DNA polymerase. Extension of the primer terminates at the first position in the PCR amplified target where a nucleotide complementary to one of the ddNTPs in the mix occurs. The primer can be annealed to a sequence either immediately 3' to or several nucleotides removed from the SNP position. For single base or single nucleotide extension assays, the primer is annealed to a sequence immediately 3' the SNP position. If the primer anneals to a sequence several nucleotides removed from the target SNP, the only limitation is that the template sequence between the 3' end of the primer and the SNP position can not contain a nucleotide of the same type as the one to be detected, or this will cause premature termination of the extension primer. Alternatively, if all four ddNTPs alone, and no dNTPs, are added to the reaction mixture, the primer will always be extended by only one nucleotide, corresponding to the target SNP position. In this instance, primers are designed to bind to a sequence one nucleotide downstream from the SNP position. In other words, the nucleotide at the 3' end of the primer hybridizes to the nucleotide immediately 3' to the SNP position. Thus, the first nucleotide added to the primer is at the SNP. In one common variation, the ddNTPs used in the assay each have a unique fluorescent label, enabling the detection of the specific nucleotide added to the primer. SNaPshot™ from Applied Biosystems is a commercially available kit for single nucleotide primer extension using fluorescent ddNTPs, and can be multiplexed. SNP-IT™ (Orchid Cellmark, Princeton, N.J.) is another commercially available product using a primer extension assay for identifying SNPs (see also U.S. Pat. No. 5,888,819). Some variations of the primer extension assay can identify heterozygotes.

An alternate detection method uses mass spectrometry to detect the specific nucleotide added to the primer in a primer extension assay. See, for instance, Haff et al. (1997, Genome Res. 7:378-388). Mass spectrometry ("mass spec") takes advantage of the unique mass of each of the four nucleotides of DNA. SNPs can be unambiguously genotyped based on the slight differences in mass, and the corresponding time of flight differences, inherent in nucleic acid molecules having different nucleotides at a single base position. MALDI-TOF (Matrix Assisted Laser Desorption Ionization-Time of Flight) mass spectrometry technology is preferred for extremely precise determinations of molecular mass, such as SNPs. Numerous approaches to SNP analysis have been developed based on mass spectrometry.

For detection by mass spectrometry, extension by only one nucleotide is preferable, as it minimizes the overall mass of the extended primer, thereby increasing the resolution of mass differences between alternative SNP nucleotides. Furthermore, mass-tagged dideoxynucleoside triphosphates (ddNTPs) can be employed in the primer extension reactions in place of unmodified ddNTPs. This increases the mass difference between primers extended with these ddNTPs, thereby providing increased sensitivity and accuracy, and is particularly useful for typing heterozygous base positions. Mass-tagging also alleviates the need for intensive sample-preparation procedures and decreases the necessary resolving power of the mass spectrometer. The primers are extended, purified and then analyzed by MALDI-TOF mass spectrometry to determine the identity of the nucleotide present at the SNP position. MassARRAY™ (Sequenom, San Diego, Calif.) is a commercially available system for SNP identification using mass spectrometry.

The primer extension assay has also been modified to use fluorescence polarization as the means of detecting the specific nucleotide at the SNP position. This modified assay is sometimes referred to as template-directed dye-terminator incorporation assay with fluorescence polarization (FP-TDI). See Kwok (2002, supra). A kit for this assay, Acycloprimer™-FP, is commercially available from Perkin Elmer (Boston, Mass.).

Allele-specific oligonucleotide ligation, also called oligonucleotide ligation assay (OLA) and is similar in many respects to ligase chain reaction, uses a pair of oligonucleotide probes that hybridize to adjacent segments of sequence on a nucleic acid fragment containing the SNP. One of the probes has a SNP allele-specific base at its 3' or 5' end. The second probe hybridizes to sequence that is common to all SNP alleles. If the first probe has an allele-specific base at its 3' end, the second probe hybridizes to the sequence segment immediately 3' to the SNP. If the first probe has an allele-specific base at its 5' end, the second probe hybridizes to the sequence segment immediately 5' to the SNP. The two probes can be ligated together only when both are hybridized to a DNA fragment containing the SNP allele for which the first probe is specific. See Landegren et al. (1988, Science 241: 1077-80). One method of detecting the ligation product involves fluorescence. The second probe, which hybridizes to either allele, is fluorescently labeled. The allele-specific probe is labeled with biotin. Strepavidin capture of the allele-specific ligation product and subsequent fluorescent detection is used to determine which SNP is present. Another variation of this assay combines amplification and ligation in the same step (Barany, 1991, PNAS 88:189-93). A commercially available kit, SNPlex™ (Applied Biosystems, Foster City, Calif.) uses capillary electrophoresis to analyze the ligation products.

Allele-specific hybridization, also called allele-specific oligonucleotide hybridization (ASO), distinguishes between two DNA molecules differing by one base using hybridization. Amplified DNA fragments containing the target SNP are hybridized to allele-specific oligonucleotides. In one variation, the amplified DNA fragments are fluorescence labeled and the allele-specific oligonucleotides are immobilized. See, for instance, Strachan et al., (1999, In: Human Molecular Genetics, Second Edition, John Wiley & Sons, New York, N.Y.). In another variation, the allele-specific oligonucleotides are labeled with a antigen moiety. Binding is detected via an enzyme-linked immunoassay and color reaction (see, for instance, Knight et al., 1999, Clin. Chem. 45: 1860-1863). In yet another variation, the allele-specific oligonucleotides are radioactively labeled (see, for instance, Saiki et al., 1986, Nature 324:163-6). Protein nucleic acid (PNA) probes and mass spec may also be used (Ross et al., 1997, Anal. Chem. 69:4197-4202).

Other SNP identification methods based on the formation of allele-specific complexes include the invasive cleavage assay and the branch migration assay. The invasive cleavage assay uses two probes that have a one nucleotide overlap. When annealed to target DNA containing the SNP, the one nucleotide overlap forms a structure that is recognized by a 5' nuclease that cleaves the downstream probe at the overlap nucleotide. The cleavage signal can be detected by various techniques, including fluorescence resonance energy transfer (FRET) or fluorescence polarization. Reaction conditions can be adjusted to amplify the cleavage signal, allowing the use of very small quantities of target DNA. Thus, the assay does not require amplication of the target prior to detecting the SNP identity, although an amplified sequence may be used. See, for instance, Lyamichev et al., 2003, Methods Mol. Biol 212:229-240; Brookes, 1999, Gene, 234:177-186; and Mein et al., 2000, Genome Res. 10:330-343). A commercially available product, the Invader® assay (Third Wave Molecular Diagnostics, Madison, Wis.), is based on this concept. The branch migration assay based on Holliday junction migration, involves the detection of a stable four-way complex for SNP identification (See, for instance, U.S. Pat. No. 6,878, 530).

SNPs can also be scored by direct DNA sequencing. A variety of automated sequencing procedures may be utilized when performing the diagnostic assays (Naeve et al., 1995, Biotechniques 19:448-453), including sequencing by mass spectrometry (see, e.g., PCT International Publication No. WO 94/16101; Cohen et al., 1996, Adv. Chromatogr. 36:127-162; and Griffin et al., 1993, Appl. Biochem. Biotechnol. 38:147-159). Traditional sequencing methods may also be used, such as dideoxy-mediated chain termination method (Sanger et al., 1975, J. Molec. Biol. 94: 441; Prober et al. 1987, Science 238: 336-340) and the chemical degradation method (Maxam et al., 1977, PNAS 74: 560).

A preferred sequencing method for SNPs is pyrosequencing. See, for instance, Ahmadian et al., 2000, Anal. Biochem, 280:103-110; Alderborn et al., 2000, Genome Res. 10:1249-1258 and Fakhrai-Rad et al., 2002, Hum. Mutat. 19:479-485. Pyrosequencing involves a cascade of four enzymatic reactions that permit the indirect luciferase-based detection of the pyrophosphate released when DNA polymerase incorporates a dNTP into a template-directed growing oligonucleotide. Each dNTP is added individually and sequentially to the same reaction mixture, and subjected to the four enzymatic reactions. Light is emitted only when a dNTP is incorporated, thus signaling which dNTP in incorporated. Unincorporated dNTPs are degraded by apyrase prior to the addition of the next dNTP. The method can detect heterozygous individuals in addition to heterozygotes. Pyrosequencing uses single stranded template, typically generated by PCR amplification of the target sequence. One of the two amplification primers is biotinylated thereby enabling streptavidin capture of the amplified duplex target. Streptavidin-coated beads are useful for this step. The captured duplex is denatured by alkaline treatment, thereby releasing the non-biotinylated strand. The detection primer used for SNP identification using pyrosequencing is designed to hybridize to a sequence 3' to the SNP. In a preferred embodiment, the 3' sequence is immediately adjacent to the SNP position. Thus, the SNP identity is ascertained when the first nucleotide is incorporated. Pyrosequencing can detect heterozygotes.

Further examples of methods that can be used to identify for the SNPs of the present invention include single-strand conformational polymorphism (SSCP) and denaturing gradient gel electrophoresis (DGGE). SSCP identifies base differences by alteration in electrophoretic migration of single stranded PCR products, as described in Orita et al., (1989, PNAS 86:2766-1770). Single-stranded PCR products can be generated by heating or otherwise denaturing double-stranded PCR products. Single-stranded nucleic acids may refold or form secondary structures that are partially dependent on the base sequence. The different electrophoretic mobilities of single-stranded amplification products are related to base-sequence differences at SNP positions. DGGE differentiates SNP alleles based on the different sequence-dependent stabilities and melting properties inherent in polymorphic DNA and the corresponding differences in electrophoretic migration patterns in a denaturing gradient gel (Myers et al., 1985, Nature 313:495 and Erlich, ed., 1992, In: PCR Technology, Principles and Applications for DNA Amplification, W. H. Freeman and Co, New York, Chapter 7).

Sequence-specific ribozymes (U.S. Pat. No. 5,498,531) can be used to score SNPs based on the development or loss of a ribozyme cleavage site. Perfectly matched sequences can be distinguished from mismatched sequences by nuclease cleavage digestion assays or by differences in melting temperature. If the SNP affects a restriction enzyme cleavage site, the SNP can be identified by alterations in restriction enzyme digestion patterns, and the corresponding changes in nucleic acid fragment lengths determined by gel electrophoresis. Immunoassay methods using antibodies specific for SNP alleles can be used for SNP detection. Southern and Northern blot analysis can also be utilized for nucleic acid analysis. See, for instance, Sambrook et al. (2001, Molecular Cloning: A Laboratory Manual, Cold Spring Harbor Laboratory Press, Cold Spring Harbor, N.Y.), Ausubel et al. (eds., 1997, Current Protocols in Molecular Biology, John Wiley & Sons, New York), and Gerhardt et al. (eds., 1994, Methods for General and Molecular Bacteriology, American Society for Microbiology, Washington, D.C.).

III. Kits Useful in the Practice of Methods of the Invention

The invention also provides a kit useful in practicing the method of the invention. The kit may contain at least one pair of amplication primers that is used to amplify a target polynucleotide sequence containing one of the four SNPs identified in the invention. The amplification primers are designed based on the sequences provided herein for the upstream and downstream sequence flanking the SNPs. In a preferred embodiment, the amplification primers will generate an amplified double-stranded target polynucleotide between about 50 basepairs to about 600 basepairs in length and, more preferably, between about 100 basepairs to about 300 basepairs in length. In another preferred embodiment, the SNP is located approximately in the middle of the amplified double-stranded target polynucleotide.

The kit may further contain a detection probe designed to hybridize to a sequence 3' to the SNP on either strand of the amplified double-stranded target polynucleotide. In one variation, the detection probe hybridizes to the sequence immediately 3' to the SNP on either strand of the amplified double-stranded target polynucleotide but does not include the SNP. This kit variation may be used to identify the SNP by pyrosequencing or a primer extension assay. For use in pyrosequencing, one of the amplification primers in the kit may be biotinylated and the detection probe is designed to hybridize to the biotinylated strand of the amplified double-stranded target polynucleotide. For use in a primer extension assay, the kit may optionally also contain fluorescently labeled ddNTPs. Typically, each ddNTP has a unique fluorescent label so they are readily distinguished from each other.

Alternatively, the kit is designed for allele specific oligonucleotide ligation. In this embodiment, in addition to the at least one pair of amplification primers, the kit may further contain a pair of detection probes that hybridize to immediately adjacent segments of sequence in one of the strands of the target polynucleotide containing the SNP. One of the two probes is SNP-allele specific; it has a SNP allele-specific nucleotide at either its 5' or 3' end. The second probe hybridizes immediately adjacent to the first probe, but is not allele specific. In one variation, the allele-specific probe is fluorescently labeled and the second probe is biotinylated, such that if the two probes are ligated, the resultant ligation product is both fluorescently labeled and biotinylated. Optionally, a third probe may be provided which is specific for the other allele of the SNP. If the optional third probe is provided, its fluorescent label may be distinguishably different from the label on the first probe.

In yet another variation, the kit is designed for a 5' nuclease assay. In this variation, in addition to the at least one pair of amplification primers, the kit may further contain at least one SNP allele-specific probe which is fluorescently labeled. The allele-specific probe may hybridize to either strand of the amplified double-stranded target polynucleotide. In a preferred embodiment, the allele-specific probe evenly straddles the SNP. That is, the SNP position is approximately in the middle of the allele-specific probe. Optionally, the kit also contains a second allele-specific probe which is specific for another allele of the SNP for which the first probe is specific. The fluorescent label on the optional second probe may be distinguishably different from the label on the first probe.

Any of the above kit variations may contain sets of primers and probes for more than one SNP position. For instance, the SNPs detected may be any combination of the four SNPs taught herein, including all four SNPs. As a non-limiting example, a kit may contain a set of primers and probes for SNP identification at each of the polymorphism at nucleotide 26 of SEQ ID NO: 1 (rs2794328), the polymorphism at nucleotide 26 of SEQ ID NO: 3 (rs446529) and the polymorphism at nucleotide 26 of SEQ ID NO: 5 (rs397559). Probes and/or primers for other SNPs diagnostic for low BMD risk may also be included. Any kit may optionally contain one or more nucleic acids that serve as a positive control for the amplification primers and/or the probes. Any kit may optionally contain an instruction material for performing risk diagnosis.

The practice of the invention is illustrated by the following non-limiting example.

EXAMPLE

Methods

Patient Ascertainment and BMD Measurements: Probands were selected who had bone mineral density Z-scores of less than −2.0 at either the lumbar spine or the femoral neck and who reported having other family members with osteoporosis. A Z-score is the number of standard deviations the patient's bone density is above or below the values expected given the patient's age. Family members were invited to the clinic for evaluation. If one or more first degree relatives of the proband had low BMD, then the proband and available family members were invited to participate. Bone mineral density was assessed by DEXA (Lunar DPX), and examination/history eliminated those with known causes (other than estrogen depletion due to menopause) of metabolic bone disease. Those families/sibpairs with at least one additional member having BMD Z-scores less than −1.0 at either the lumbar spine or the femoral neck were selected for genetic analysis. The total population consisted of six large multi-generational families (Devoto et al., 1998, Eur J Hum Genet 6:151-157), 24 nuclear families with two to four children and six three-generation families with two sibships of two to four offspring (Devoto et al., 2001, Hum Molec Genet 10: 2447-2452). Two families of two sisters each without parents that were included in the 2001 work were excluded from the present analysis because X-chromosome microsatellite marker genotypes were inconsistent with a sibling relationship. Thus, a cohort of 40 osteoporosis families was used in the study.

Genotypin: Using the PureGene® DNA Isolation Kit (Gentra Systems, Minneapolis, Minn.) genomic DNA was extracted from blood directly, or from lymphoblast cultures established from patients' lymphocytes by EBV transformation. Whole Genome Amplification was performed using a GenomiPhi™ DNA amplification kit (Amersham Biosciences, Piscataway, N.J.). Amplified DNAs were validated prior to genotyping (Frenck Holbrook et al, J. Biomol. Techn. 16:125-133 (2005)). Two methods were used for SNP genotyping: Assays-On Demand™, which is a commercially available 5' nuclease assay, and pyrosequencing.

i. Assays-On Demand™: SNP genotyping was performed on the ABI 7900HT Sequence Detection System using inventoried Assays-on-Demand™ for the single nucleotide polymorphisms in or near genes CAMTA1, GNB1, ICMT, and SHREW1 and the intergenic single nucleotide polymorphism near WDR8. PCRs were performed and analyzed on the ABI 7900HT (Applied Biosystems, Foster City, Calif.) according to the manufacturer's specification. Assays were arrayed on a 384-well optical plate using 25 ng of DNA in a 5 microliter (μl) reaction volume. Briefly, 25 ng (1 μl) of genomic DNA was incubated with 2.5 μl of 2×Taq Man Master Mix (with Amperase), 0.25 μl of 20× Assays on Demand, and 1.25 μl Water. Reactions were set-up in 384 well plates and assayed on the ABI7900 real time instrument using Absolute Quantitation Run conditions as follows:
1. 50° C. 2 min
2. 95° C. 10 min
3. 50 cycles of:
   95° C. 15 sec
   60° C. 1 min Data were analyzed using SDS 2.1 software (Applied Biosystems, Foster City, Calif.).

ii. Pyrosequencing: WDR8 was screened using 7 SNPs that were assessed by pyrosequencing. Specific amplification primer pairs (listed in Table 2 as "F" and "R") were used to amplify the SNP containing regions of this gene. For each primer pair, one of the primers was biotinylated (e.g. "F-biotin") to allow subsequent immobilization of PCR products onto Streptavidin Sepharose™ HP (GE Healthcare, Amersham Pharmacia Biotech, Uppsala, Sweden). Specific dection primers, designed to hybridize to sequence immediately 3' to the SNP of interest, were then annealed to the single-stranded biotinylated templates, and the samples subjected to pyrosequencing using the PSQ96 SNP Reagent Kit (Pyrosequencing AB, Uppsala, Sweden), following the manufacturer's recommendation.

TABLE 2

| SNP ID | Primer code[1] | SEQ ID NO. | Primer sequence |
|---|---|---|---|
| rs3818330 | F-biotin | 9 | 5'-CAAGGACCAGACGGTTATC-3' |
| | R | 10 | 5'-GATCCACTCCAGCAGTCAG-3' |
| | SNP | 11 | 5'-AGACGGTCTCTGATGATG-3' |
| rs2296034 | F | 12 | 5'-TGCACTGGTTCCCACCTTTC-3' |
| | R-biotin | 13 | 5'-TTGTTGTCCACGTACAGCG-3' |
| | SNP | 14 | 5'-ACAGACTTGAGCCCA-3' |
| rs3765689 | F-biotin | 15 | 5'-GTGAGCGTCTGTGTGTAATG-3' |
| | R | 16 | 5'-GGCAGGATTACAATGATTCC-3' |
| | SNP | 17 | 5'-CTAAATGATACTGCAGTT-3' |
| rs1004650 | F | 18 | 5'-CTGGTGTACGTGGTCGAGG-3' |
| | R-biotin | 19 | 5'-CTTGGAGTTGTTCTCTGCG-3' |
| | SNP | 20 | 5'-GGGCGGGGCGGCGGGT-3' |
| rs2251098 | F-biotin | 21 | 5'-AAGTCAGAAGGCGGAAGTG-3' |
| | R | 22 | 5'-ACGTGGGCGTTTCCTTTAAAGC-3' |
| | SNP | 23 | 5'-CAATGCCGCGCGGAAG-3' |
| rs2760320 | F-biotin | 24 | 5'-CCGACAGAGCAAACCCGAAA-3' |
| | R | 25 | 5'-CAGGACACAGTAAAGGGTGAG-3' |
| | SNP | 26 | 5'-CCAGCATTCCTATGCC-3' |
| rs1885864 | F-biotin | 27 | 5'-CCCCTTTCGCAGACATCATA-3' |
| | R | 28 | 5'-GACCACAGTGACTCAAGACAAC-3' |
| | SNP | 29 | 5'-CAGACCCCTTCCAGCC-3' |

Note
[1]"F": forward primer used in the PCR reaction; "R": reverse primer used in the PCR reaction; "SNP": detection primer used during the pyrosequencing; "Biotin": primer that was biotinylated.

Statistical analysis: Patterns of linkage disequilibrium between the SNP alleles and the putative trait locus have been investigated using a quantitative transmission disequilibrium test (QTDT). The QTDT is not affected by the presence of population stratification, which may confound the results obtained from population based association studies. QTDT analysis was performed in the DNA cohort using the QTDT program (Abecasis et al, 2000, Eur. J. Hum. Genet. 8(7):545-51; Abecais et al., 2000, Am. J. Hum. Genet. 66(1):279-292)]). The orthogonal model included in the QTDT software was applied to data from the cohort of 40 families. In this model, the contribution of the tested marker to the total phenotypic mean is decomposed into a between family (b) component and a within family (w) component. A test of significant deviation of w from 0 is a test of association between the marker and the trait, independent of population stratification. QTDT allows the use of multiallelic markers or haplotypes, and for covariates to be included in the model, such as age, BMI, and sex. Those SNPs that show significant association with BMD with p-values of less than 0.05 are considered as markers for the identification of candidate genes or regions to be subject to further genetic and/or functional analysis in future studies. The SNPs with significant association (p<0.1) with FN-BMD, LS-BMD or T-BMD are themselves useful as predictive indicators of risk of low BMD and, consequently, as predictors of risk of osteoporosis.

Results

A whole genome linkage analysis was performed using bone mineral density (BMD) data collected at the femoral neck (FN), lumbar spine (LS) and trochanter (T) in the cohort of 40 osteoporosis families in the present study. Evidence for quantitative trait loci (QTLs) influencing BMD was observed for chromosomes 1, 2, 4, 5, 12, 22, and X. The region that received the strongest support from variance component linkage analysis was chromosome 1p36, with a maximum lod-score of 2.96 near marker DIS2694 for femoral neck BMD. Fine mapping of 1p36 gave further support to a region near marker DIS214 from both linkage (max lod=3.5) and linkage disequilibrium analysis (p<0.01).

In the present study, five genes from the 1p36 region were selected to conduct SNP genotyping of the osteoporosis cohort. The five genes are guanine nucleotide binding factor 1 (GNB1; bp1,748,892 to bp1,854,657), WD repeat domain 8 (WDR8; bp3,570,497 to bp3,589,794), SHREW1 (bp4,625,478 to bp4,754,223), isoprenylcysteine carboxyl methyltransferase (ICMT; bp6,215,521 to bp6,230,298) and calmodulin binding transcription activator 1 (CAMTA1; bp6,779,650 to bp7,7621,169). The basepair numbering indicated was obtained from the National Center for Biotechnology Information (NCBI) Entrez Gene database as of the Jun. 7, 2005 update.

These five genes are within a 7 MB region of 1p36 and were selected based on their possible functional relevance to bone biology. Data were analyzed using QTDT to look for evidence of linkage disequilibrium between the candidate gene SNP alleles and the BMD traits. A total of 37 SNPs were tested in or near the 5 genes. In GNB1, 10 SNPs were tested. In WRD8, 7 SNPs were tested. In SHREW1, 6 SNPs were tested. In CMT, 2 SNPs were tested. Ten SNPs were tested in CAMTA1. A SNP in an intergenic region near WRD8 was tested, and a SNP in RPL22, near ICMT, was also tested. Results of the analysis of 17 of the 37 SNPs are summarized in Table 3.

TABLE 3

| SNP ID | SNP Locus | Nominal p-value | | |
|---|---|---|---|---|
| | | FN-BMD | LS-BMD | T-BMD |
| rs2794328 | Intergenic region near WDR8 | 0.01 | >0.1 | 0.05 |
| rs2760320 | WDR8-Ex 11 | >0.1 | >0.1 | >0.1 |
| rs2296034 | WDR8-Ex 8 | >0.1 | >0.1 | >0.1 |
| rs1885864 | WDR8-In 5 | >0.1 | >0.1 | >0.1 |
| rs3818330 | WDR8-In 4 | >0.1 | >0.1 | >0.1 |
| rs3765689 | WDR8-In 4 | >0.1 | >0.1 | >0.1 |
| rs2251098 | WDR8-5'UTR | >0.1 | >0.1 | >0.1 |
| rs1004650 | WDR8-5'UTR | >0.1 | >0.1 | >0.1 |
| hcv1944289 | SHREW1-In 1 | >0.1 | >0.1 | >0.1 |
| rs7514522 | SHREW1-In 2 | >0.1 | >0.1 | >0.1 |
| rs242056 | SHREW1-Ex 3 | >0.1 | >0.1 | >0.1 |
| rs446529 | SHREW1-In 3 | 0.02 | 0.08 | >0.1 |
| rs397559 | SHREW1-In 3 | 0.03 | >0.1 | >0.1 |
| rs414909 | SHREW1-In 7 | >0.1 | >0.1 | >6.1 |
| rs2294714 | RPL22-In 1 | >0.1 | >0.1 | >0.1 |
| rs14281 | ICMT Ex7 3'UTR | >0.1 | >0.1 | >0.1 |
| rs1802353 | ICMT 3'UTR | >0.1 | 0.03 | 0.07 |

Quantitative transmission disequilibrium test (QTDT) of 17 SNPs located in or near three of the five candidate genes selected from the lp36 region. SNPs position in the candidate genes and flanking intergenic region are as reported in the NCBI and the Celera databases. Hcv1944289 is a DNA variant found uniquely in the Celera database. In, Intron; Ex, Exon; UTR, untranslated region; FN, Femoral Neck; LS, Lumbar Spine; T, Trochanter.

Quantitative transmission disequilibrium test (QTDT) of 17 SNPs located in or near three of the five candidate genes selected from the 1p36 region. SNPs position in the candidate genes and flanking intergenic region are as reported in the NCBI and the Celera databases. Hcv1944289 is a DNA variant found uniquely in the Celera database. In, Intron; Ex, Exon; UTR, untranslated region; FN, Femoral Neck; LS, Lumbar Spine; T, Trochanter.

Results of the QTDT analysis were not significant (all p-values >0.1) for the 10 SNPs tested in GNB1 or for the 10 SNPs tested in CAMTA1, therefore these data are not included. As shown in Table 3, the 7 SNPs located in WDR8, 4 of the 6 SNPs in SHREW1, the SNP in RPL22 and 1 of the 2 SNPs in ICMT were also not significantly associated with low BMD (all p-values >0.1).

The SNP located in the intergenic region near WDR8, rs2794328, had a nominal p-value of p=0.01 for association with femoral neck BMD and p=0.05 for association with trochanter BMD. One SNP in ICMT, rs1802353, yielded a p-value of 0.03 for spine BMD and 0.07 for trochanter BMD, but displayed no significant association with femoral neck BMD. In the last gene tested, SHREW1, two of the six SNPs, rs446529 and rs397559, yielded p values of 0.02 and 0.03 with femoral neck BMD. One of these SNPs, rs446529, also yielded a p-value of 0.08 for association with spine BMD. Both of these SNPs are located in intron 3 of SHREW1. They are 25,385 bp apart from each other.

All references discussed herein are incorporated by reference. One skilled in the art will readily appreciate that the present invention is well adapted to carry out the objects and obtain the ends and advantages mentioned, as well as those inherent therein. The present invention may be embodied in other specific forms without departing from the spirit or essential attributes thereof and, accordingly, reference should be made to the appended claims, rather than to the foregoing specification, as indicating the scope of the invention.

What is claimed is:

1. A method of diagnosing risk of low femoral neck bone mineral density (BMD) or low trochanter BMD in a Caucasian human being said method comprising: detecting the identity of at least one chromosome 1p36 polymorphism in a biological sample from a Caucasian human being, wherein said at least one chromosome 1p36 polymorphism is an "A" at nucleotide 26 of SEQ ID No: 1 or a "T" at nucleotide 26 of the corresponding minus strand of SEQ ID NO: 1 and diagnosing risk of low femoral neck BMD or low trochanter BMD in said Caucasian human being when the said at least one chromosome 1p36 polymorphism is detected.

2. The method of claim 1 wherein said risk of low femoral neck BMD is diagnosed.

3. The method of claim 1 wherein said risk of low trochanter neck BMD is diagnosed.

4. A method of diagnosing risk of osteoporosis in a Caucasian human being said method comprising: detecting the identity of at least one chromosome 1p36 polymorphism in a biological sample from a Caucasian human being, wherein said at least one chromosome 1p36 polymorphism is an "A" at nucleotide 26 of SEQ ID No: 1 or a "T" at nucleotide 26 of the corresponding minus strand of SEQ ID NO: 1 and diagnosing risk of osteoporosis in said Caucasian human being when the said at least one 1p36 chromosome polymorphism is detected.

* * * * *

UNITED STATES PATENT AND TRADEMARK OFFICE
CERTIFICATE OF CORRECTION

| | |
|---|---|
| PATENT NO. | : 7,618,779 B2 |
| APPLICATION NO. | : 11/232609 |
| DATED | : November 17, 2009 |
| INVENTOR(S) | : Marcella Devoto et al. |

It is certified that error appears in the above-identified patent and that said Letters Patent is hereby corrected as shown below:

Title Page, (*) Notice: Subject to any disclaimer, the term of this patent is extended or adjusted under 35 U.S.C. 154(b) by 237 days.

should read (*) Notice: Subject to any disclaimer, the term of this patent is extended or adjusted under 35 U.S.C. 154(b) by 554 days.

Signed and Sealed this

Fourth Day of May, 2010

David J. Kappos
*Director of the United States Patent and Trademark Office*